(12) United States Patent
Popescu

(10) Patent No.: US 7,209,537 B2
(45) Date of Patent: Apr. 24, 2007

(54) X-RAY TOMOGRAPHY APPARATUS AND OPERATING METHOD FOR GENERATING MULTIPLE ENERGY IMAGES

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/257,694

(22) Filed: Oct. 25, 2005

(65) Prior Publication Data

US 2006/0109951 A1 May 25, 2006

(30) Foreign Application Priority Data

Oct. 25, 2004 (DE) .................... 10 2004 051 820

(51) Int. Cl.
*A61B 6/00* (2006.01)
*H06G 1/44* (2006.01)

(52) U.S. Cl. ........................ 378/16; 378/108

(58) Field of Classification Search ................ 378/16, 378/108–112, 145; 250/505.1
See application file for complete search history.

(56) References Cited

U.S. PATENT DOCUMENTS

| 5,822,393 A | 10/1998 | Popescu |
| 6,507,639 B1 | 1/2003 | Popescu |
| 2003/0048873 A1* | 3/2003 | Dinten et al. ............. 378/108 |
| 2004/0101087 A1 | 5/2004 | Hseih et al. |
| 2005/0195939 A1* | 9/2005 | Scheinman et al. ........... 378/57 |

OTHER PUBLICATIONS

"Upright Image Reader That Supports Energy Subtraction Processing Software," Chikugo et al., Fuji Computed Radiography Technical Review, No. 12 (2000).
Image Quality Guide for Somatom Plus/Plus-S, Siemens AG.
"The Challenges of Direct Digital X-ray Detectors," www/dondickson.co.uk. Mar. 30, 2003.
"Technology and Image Results of a Spectral CT System," Heismann et al., Siemens Medical Solutions, Computed Tomography Detector Center.

* cited by examiner

*Primary Examiner*—Akm Ullah
*Assistant Examiner*—Anthony Cochran
(74) *Attorney, Agent, or Firm*—Schiff Hardin LLP

(57) ABSTRACT

In a tomography apparatus and a method for operating a tomography apparatus for generation of multiple energy images, in which high-energy projections and low-energy projections are acquired by alternating adjustment of a voltage and a further control variable (namely the current or the exposure time), given a set first voltage value and a set first control value of the further control variable, and given a set second voltage value and a set second control value of the further control variable, x-rays generated by an x-ray radiator exhibit essentially the same x-ray dose or photon flow.

46 Claims, 6 Drawing Sheets

FIG 2
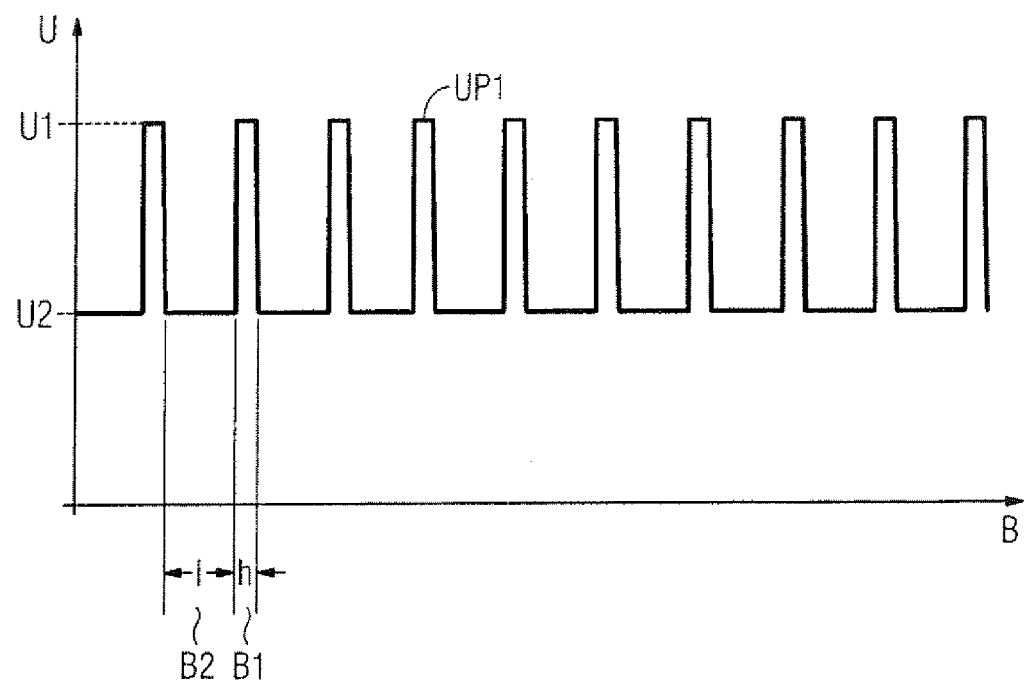
FIG 3
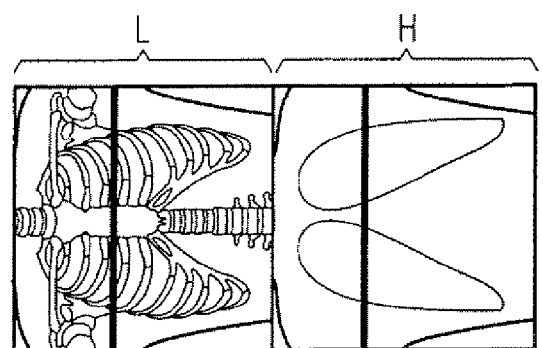
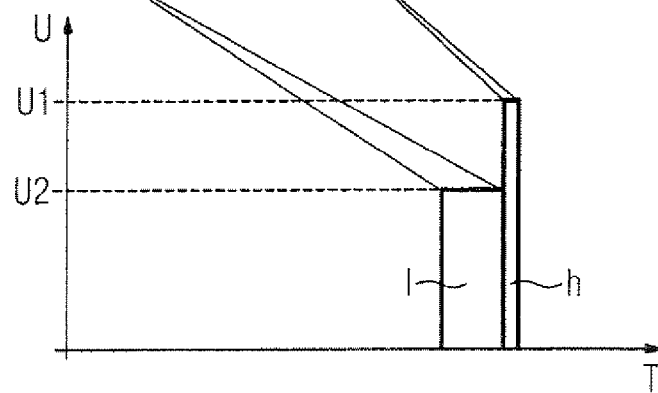

| R        φ | b1    | b2      | b3      |
|---|---|---|---|
| $R_n$     | h     | l       | h       |
| $R_{n+1}$ | l     | h       | l       |
| $R_{n+2}$ | h     | l       | h       |
| $R_{N+3}$ | l     | h       | l       |
| ...       |       |         |         |

|  | 1-120 | 121-240 | 241-360 |

X-RAY TOMOGRAPHY APPARATUS AND OPERATING METHOD FOR GENERATING MULTIPLE ENERGY IMAGES

BACKGROUND OF THE INVENTION

1. Field of the Invention

The present invention concerns an x-ray tomography apparatus for generation of multiple energy images and a method for generation of multiple energy images with such a tomography apparatus.

2. Description of the Prior Art

"Multiple energy images," are x-ray images that are generated with different x-ray energies. For example, by a weighted subtraction on the basis of a low-energy image and a high-energy image it is possible to calculate images in which essentially only substances with a specific absorption characteristic are still visible. This fact is in particular used in diagnostic medicine for visualization of soft tissue separate from bony tissue. Multiple energy images can be generated in different manners.

In FujiFilm Co., Technical review no. 12, "Upright image reader that supports energy subtraction processing software", an x-ray apparatus is described that enables the simultaneous generation of a low-energy image and a high-energy image with a fixed, set energy of the x-ray radiation by means of an energy-selective detector. The energy-selective detector has two detector arrays disposed in series, between which is arranged an absorption filter in the form of a copper filter for reduction of the energy of the x-ray radiation. Such detectors are very expensive to produce due to the use of two separate detector arrays. Moreover, with such a detector the achievable energy difference of the x-ray radiation used for generation of the high-energy image and of the low-energy image is very slight, such that bony tissue and soft tissue cannot always be completely separated in the calculated images.

Furthermore, a tomography apparatus is known from United States Patent Application Publication No. 2004/0101087 with which the low-energy image and the high-energy image can be generated via two separate exposures at different energies of the x-ray radiation. The different energies of the x-ray radiation are set by different voltages. The low-energy image is detected at a set voltage value of 80 kV and the high-energy image is detected at a set voltage value of 160 kV.

Given the same current values, dependent on the set voltage values the x-ray radiation exhibits a different x-ray dose or flux. Due to the equivalence of x-ray dose and flux, the following statements representative for both terms but only the term x-ray dose is used. Table 1 exemplarily shows the relation between the voltage and the relative x-ray dose. The x-ray dose is normalized relative to a set voltage value of 140 kV:

TABLE 1 voltage vs. relative x-ray dose

| Voltage | Relative x-ray dose |
|---|---|
| 140 kV | 100% |
| 120 kV | 40% |
| 80 kV | 20% |

The x-ray dose at a voltage value of 140 kV (which is, for example, used for generation of the high-energy image) is accordingly approximately 5 times higher than the x-ray dose at a voltage value of 80 kV (which is used for generation of the low-energy energy). The patient is exposed to a different radiation exposure given the generation of high-energy images and low-energy images.

SUMMARY OF THE INVENTION

An object of the present invention is to provide a tomography apparatus and a method for operating a tomography apparatus that enable, in a simple manner, generation of multiple energy images with essentially the same x-ray dose of an x-ray beam.

This object is achieved by a tonography apparatus wherein a first adjustment of the voltage is made between a first voltage value for detection of high-energy projections and a second voltage value differing therefrom this for detection of low-energy projections, and a second adjustment of a further control variable is made between a first control value and a second control value differing therefrom. The setting of the first control value ensues dependent on the first voltage value and the setting of the second control value ensues dependent of the second voltage value, such that the respectively generated x-ray radiation exhibits an essentially identical x-ray dose or photon flow.

The alternating adjustment of two control variables (namely the voltage and a further control variable) between the first voltage value and the second voltage value, and between the first control value of the further control variable and the second control value of the further control variable, can be implemented with little effort, such that a detection of high-energy projections and low-energy projections is possible without significant modifications.

The generation of the projections ensues according to the invention with essentially equal x-ray doses, such that high-energy projections and low-energy projections can be acquired with an essentially identical image quality given simultaneous low radiation exposure of a subject, i.e. a patient.

The adjustment of the voltage ensues between a first voltage value that is always the same and a second voltage value that is always the same. The respective control values of the further control variable for generation of identical x-ray doses must merely be determined and established once at the beginning of the startup of the tomography apparatus or of the method. An elaborate dynamic modulation of the x-ray radiation or of the current of the x-ray tube, such as are known from U.S. Pat. Nos. 6,507,639 B1 and 5,822,393 is not necessary.

An exposure time that can be adjusted quickly and in a simple manner in an alternating fashion is advantageously provided as a further control variable. The adjustment of the exposure time is achieved with a substantially constant current.

In addition to the exposure time, a current that can be adjusted by a simple regulation electronic is also provided. The adjustment of the current ensues with a substantially constant exposure time.

In an embodiment of the invention, the detection of the high-energy projections and the low-energy projections ensues by an alternating adjustment of the voltage and the exposure time with simultaneous displacement of the subject region and the acquisition system relative to one another, such that high-energy images and low-energy images are generated in the form of topograms. The adjustment of the voltage can ensue, for example, such that image lines of the high-energy image and of the low-energy image are acquired in alternating fashion. High-energy images and low-energy images thus can be generated in a single scan procedure.

In an embodiment of the invention, an alternating adjustment of the voltage and the current occurs with a displacement of the subject region and of the acquisition system relative to one another and additionally with rotation of the acquisition system, such that the subject region is scanned in a spiral fashion.

The alternating adjustment of voltage and current preferably ensues such that a number of successive high-energy projections can be acquired given a set first voltage value and a set first current value and a number of successive low-energy projections can alternately be acquired at different angular ranges of the rotating acquisition system given a set second voltage value and a set second current value. Given such an adjustment, voltage and current respectively exhibit unaltered control values for an entire angular range (for example 120 degrees), such that conventional x-ray radiators in the form of x-ray tubes that exhibit a delayed switching behavior between the first and second current value can also be used for generation of high-energy projections and for generation of low-energy projections.

So that high-energy projections also can be calculated in the angular ranges in which only low-energy projections are detected, the adjustment of voltage and current occurs such that, in two successive rotations, high-energy projections are acquired during the second rotation in those angular ranges in which low-energy projections were previously acquired in the first rotation.

For each acquired low-energy projection, a high-energy projection then can be interpolated from different rotations on the basis of high-energy projections acquired in the same angular ranges. A particularly simple interpolation is to average the projections respectively acquired at adjacent scan positions, which projections were acquired in essentially the same angular ranges. The greater the overlap of projections from two adjacent rotations, or the smaller the geometric offset of the acquired image information of the subject region, the smaller the interfering artifacts in the respective interpolated projection.

In reverse, low-energy projections in the angular regions in which high-energy projections are acquired can then be calculated particularly simply when the adjustment of voltage and current is effected such that, given two respective, successive rotations, low-energy projections are acquired in the second rotation in those angular ranges in which high-energy projections were previously acquired in the first rotation.

A low-energy projection on the basis of low-energy projections acquired in essentially the same angular ranges can be calculated from different rotations corresponding to each high-energy projection.

In a further embodiment of the invention, an alternating adjustment of the voltage and of the exposure time occurs with a spiral scanning, thus a displacement of the subject region and of the acquisition system relative to one another while rotating the acquisition system.

In an alternating fashion, one of the high-energy projections is acquired at an adjusted first voltage value and an adjusted first exposure time, and one of the low-energy projections is acquired at an adjusted second voltage value and adjusted second exposure time. Adjustment of the control variables after each projection, rather than after rotation around an entire angular range, can likewise be conducted with conventional x-ray tubes in which the exposure time can be adjusted just as quickly as the voltage.

Starting from the set first voltage value and the set first exposure time of the high-energy projections, a direct adaptation of the voltage to the second voltage value and to the second exposure time is in the subsequent low-energy projections. In reverse, starting from the set second voltage value and a set second exposure time a direct adaptation of the voltage to the first voltage value and to the first exposure time likewise is used in the following low-energy projections. Given such an adjustment, at least given a change of the projections, the voltage must only be adjusted by the difference between the first voltage and the second voltage, such that in a simpler operation of the high-voltage generator is achieved.

Moreover, the adjustment of the voltage and of the exposure time can be conducted such that the first exposure time can be centered on a first set voltage value and the second exposure time can be centered on a set second voltage value with regard to a time interval of a projection. With this alignment with regard to the time interval of a respective projection, it is ensured that all projections are acquired at equidistant angular intervals.

In an embodiment of the invention, a low-energy projection on the basis of low-energy projections of the same rotation, acquired at adjacent scan positions, can be interpolated for each high-energy projection. In the simplest case, the interpolation is averaging of the corresponding low-energy projections.

A high-energy projection on the basis of high-energy projections of the same rotation, acquired at adjacent scan positions, can be interpolated for each low-energy projection. In the simplest case, the interpolation is averaging of the corresponding high-energy projections.

A low-energy image or a high-energy image can be calculated according to a known reconstruction method on the basis of the acquired and interpolated low-energy projections and high-energy projections.

Further images can be calculated from the high-energy image and the low-energy image:

A soft tissue image that essentially shows only the tissue of soft parts and no osseous tissue can be calculated according to the following rule:

$$W = a*H - L,$$

wherein H is the high-energy image, L is the low-energy image, a is a first weighting coefficient of the high-energy image and W is the soft-tissue image. The weighting factor a can exhibit a value of 1.5.

An Osseous tissue image that essentially shows only bony tissue and no soft tissue can be calculated according to the following rule:

$$K = L - b*H,$$

wherein H is the high-energy image, L is the low-energy image, b is a second weighting coefficient of the high-energy image and K is the bony tissue image, The weighting factor b can exhibit a value of, for example, 1.25.

An additive image that can be calculated by addition of the high-energy image and the low-energy image can be calculated as well.

DESCRIPTION OF THE DRAWINGS

FIG. 2 illustrates alternating adjustment of voltage and exposure time in the tomography apparatus of FIG. 1, in the form of a first signal profile for generation of multiple energy images in the form of topograms.

FIG. 3 shows the relation between projections and image lines of the multiple energy images given the alternating adjustment of voltage and exposure time of FIG. 2.

DESCRIPTION OF THE PREFERRED EMBODIMENTS

Figure 1:
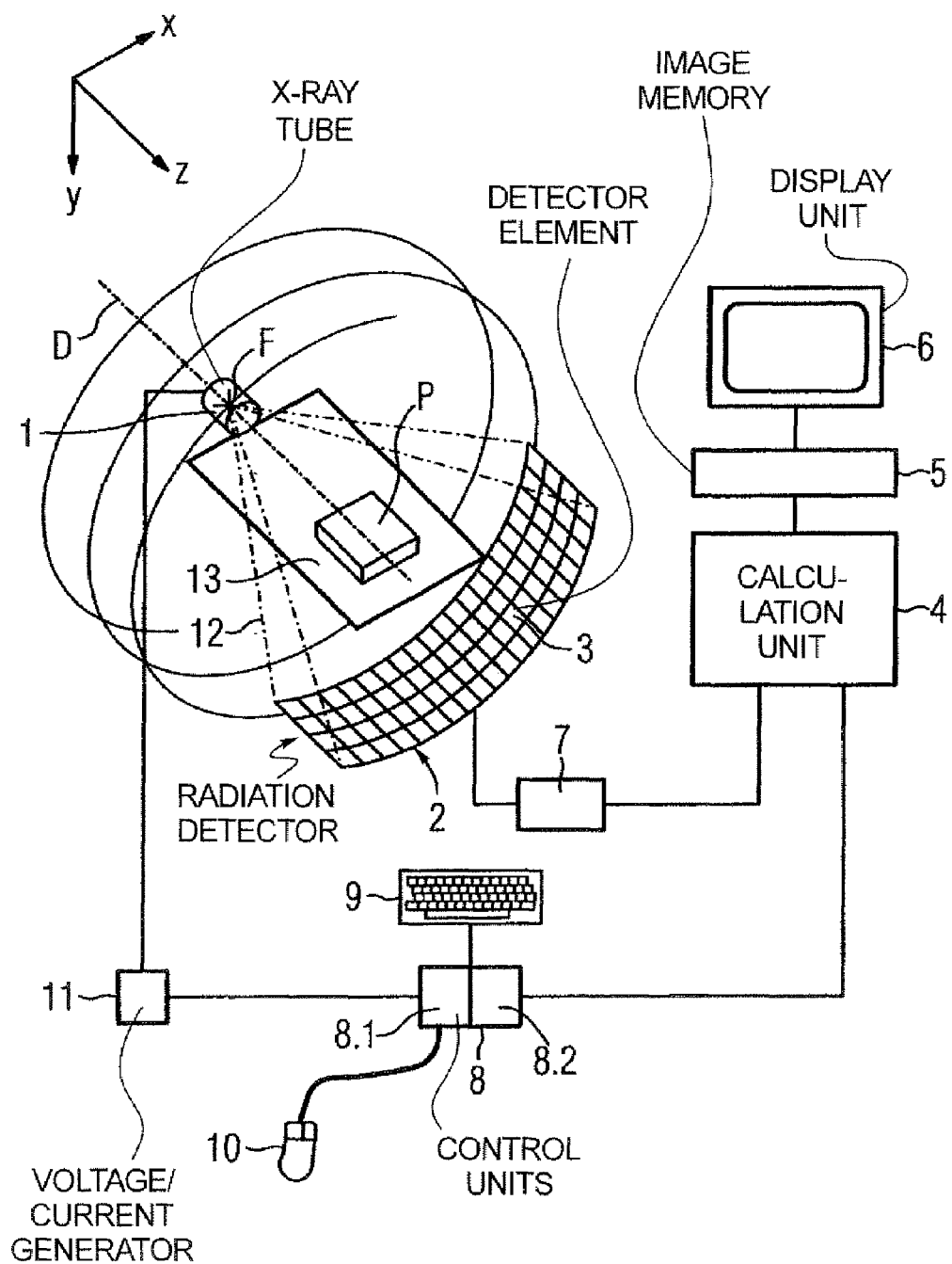
FIG. 1 is a perspective and block diagram schematic illustration of an inventive tomography apparatus for generation of multiple energy images.

An inventive tomography apparatus, here in the form of a computed tomography apparatus, is shown in FIG. 1. The computed tomography apparatus includes: an x-ray radiator in the form of an x-ray tube 1, a radiation detector 2 composed of detector elements 3 in columns and rows in a detector array, an adjustment device 8 having a first control unit 8.1 for alternating adjustment of a voltage and a second control unit 8.2 for alternating adjustment of a further control variable; a calculation unit 4 for preparation of the acquired projections and for calculation of diverse result images (for example a low-energy image and a high-energy image in the form of slice images or topograms); an image memory 5; and a display unit 6.

The x-ray tube 1 and the radiation detector 2 are part of an acquisition system and are mounted opposite one another on a rotary frame (not shown) such that x-rays emanating from a focus F of the x-ray tube 1 and limited by edge rays 12 strike the radiation detector 2.

The tomography apparatus has a measurement table 13 for supporting a subject or a subject region P. The measurement table 13 can be displaced relative to the acquisition system 1, 2 in the direction of the z-axis of a Cartesian coordinate system shown in FIG. 1. In this manner, high-energy images and low-energy images can be produced, each in the form of a topogram given a continuous displacement of the subject region P, with a rotary angle position of the acquisition system, with operation according to the invention.

In addition to the displacement of the subject region P in the direction of the z-axis relative to the acquisition system, the acquisition system can be rotated around a system axis D by means of an actuation device (not shown). The system axis D runs parallel to the z-axis. Rotation of the acquisition system given a simultaneous feed of the measurement table 13 allows a spiral scan of the subject region P, such that, with operation according to the invention, high-energy images and low-energy images can be produced in the form of slice or volume images.

The x-ray tube 1 is operated to emit x-rays by a voltage current generator 11, which generates a predetermined voltage, a predetermined current and a predetermined exposure time. The adjustment device 8 is connected with the voltage current generator 11 and enables the alternating adjustment of the voltage by means of the first control unit 8.1 and the adjustment of the further control variable by means of the second control unit 8.2. The adjustment of the voltage ensues in an alternating fashion between a first high voltage value (for example 140 kV) for generation of high-energy projections and a second low voltage value (for example 80 kV) for generation of low-energy projections. The setting of the first control variable respectively ensues dependent on the voltage between a first control value and a second control value, such that the x-ray radiation essentially exhibits an equal x-ray dose at the various voltage values. The further control variable (adjustable by the second control unit 8.2) can alternatively be the current or the exposure time.

The high-energy projections and low-energy projections generated by the detector 2 at different voltage values and thus different energies of the x-ray radiation are acquired by an acquisition module 7 and supplied to the calculation unit 4. The calculation unit 4 processes the high-energy projections and the low-energy projections into result images, for example into a high-energy image and a low-energy image that is stored in an image memory 5 in connection with the calculation and is visualized via a display unit 6. The adjustment device 8 can be operated in various operating modes that can be selected by operating personnel by a keyboard 9 or a mouse 10.

A first operating mode serves for detection of multiple energy images in the form of topograms. The alternating adjustment of voltage and exposure time ensues with a substantially constant current of the x-ray tube and given a hard-set rotary angle position of the acquisition system 1, 2, and with a simultaneous displacement of the subject region P in the direction of the system axis D. One of the high-energy projections is acquired at a set first voltage value and a set first exposure time and one of the low-energy projections is acquired at a set second voltage value and a set second exposure time, the high-energy projections and low-energy projections being acquired in alternating fashion. Each projection is associated with an image line in the corresponding energy image. The high-energy and low-energy images can be generated in this manner, synchronized with a continuous displacement of the subject region P in the direction of the system axis D.

FIG. 2 shows alternating adjustment of voltage and exposure time in the form of a first signal profile UP1 for generation of multiple energy images in the form of topograms. For simplified representation, only one high-energy projection h and one low-energy projection l are shown and provided with reference characters. In this example, the voltage U and the exposure time B are adjusted in alternating fashion between a first voltage value U1 of 140 kV and a first exposure time B1 with 2 ms for generation of a high-energy projection h and a second voltage value U2 of 90 kV and a second exposure time B2 of 8 ms for generation of a low-energy projection l.

The control values U1, U2, B1, B2 of voltage U and exposure time B are thereby selected such that the x-ray radiation exhibits an essentially equal x-ray dose both for low-energy projections l and for high-energy projections h. The speed of the displacement of the subject region in the direction of the system axis is selected such that essentially the same partial section of the subject region to be examined is scanned by the respective high-energy projection h and by the respective low-energy projection l in a time interval of 10 ms.

As an example, FIG. 3 shows the relation between a high-energy projection h and an image line in the high-energy image H and the association between a low-energy projection l and an image line in the low-energy image L in the case of an alternating adjustment of voltage U and exposure time B from FIG. 2, with a simultaneously shifting of the subject region P. The high-energy image H and the low-energy image L can be generated in this manner in step with a continuous displacement of the subject region P.

A second operating mode serves for acquisition of multiple energy images in the form of slice or volume images. In a first exemplary embodiment, the further adjustment variable is the current. The adjustment of voltage and current ensues with a substantially constant exposure time and with simultaneous feed of the subject region and with simultaneous rotation of the acquisition system of the computed tomography apparatus shown in FIG. 1, such that the subject region is scanned in a spiral manner. The adjustment device is operated such that a number of successive high-energy projections can be acquired at a set first voltage value and a set first current value, and a number of successive low-energy projections can be acquired at a second set voltage value and a set second current value. The high-energy projections and low-energy projections can be alternately acquired in different angular ranges of the rotating acquisition system. Voltage values and current values are selected such that the x-ray radiation for high-energy projections and for low-energy projections essentially exhibits the same x-ray dose.

Figures 4, 5:
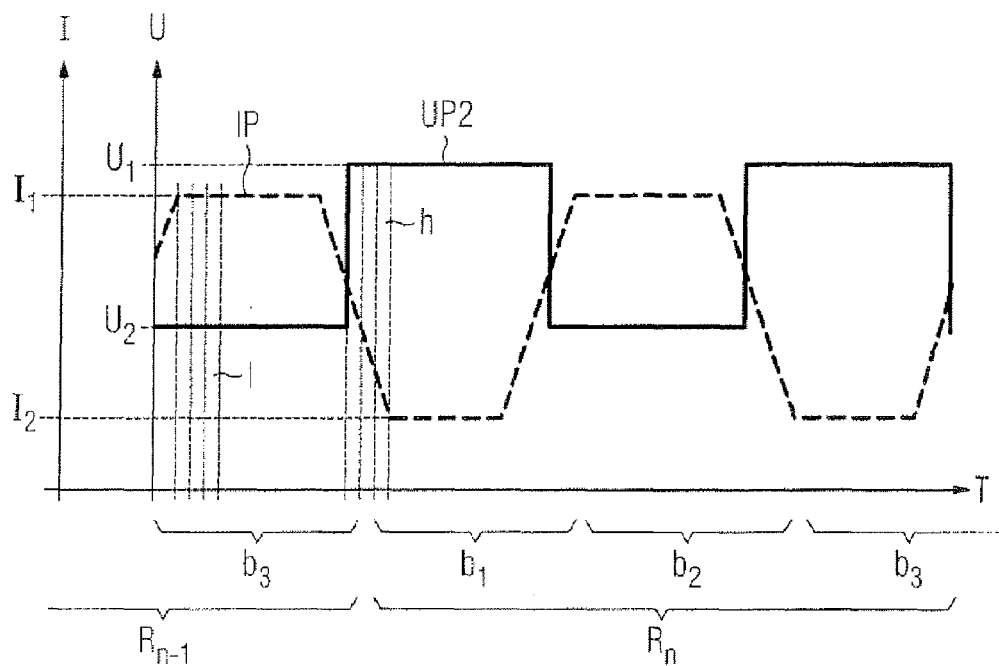
FIG. 4 illustrates alternating adjustment of voltage and current in the tomography apparatus of FIG. 1, in the form of a second signal profile for generation of multiple energy images in the form of slice or volume images.
FIG. 5 shows a sequence of low-energy and high-energy projections for different rotations in tabular form for the alternating adjustment of voltage and current of FIG. 4.

The alternating adjustment of voltage U and current l in the form of a second signal profile of the voltage UP2 and a signal profile of the current IP for generation of multiple energy slice images in the form of slice or volume images is shown in FIG. 4. Voltage U and current l respectively exhibit unaltered control values U1, l1 or, respectively, U2, l2 for an entire angular range b1 or, respectively, b2 or, respectively, b3 of, for example, 120 degrees. Such an operating mode of the tomography apparatus is particularly advantageous for x-ray tubes exhibiting a delayed adaptation behavior between the first current value l1 and the second current value l2. In this example, the generation of a high-energy projection h ensues at a set first voltage value U1 of 140 kV and at a set first current value l1 of 100 mA. In contrast, a low-energy projection l ensues at a set second voltage value U2 of 80 kV and at a set second current value l2 of 500 mA. In both projections h, l, the x-ray radiator exhibits approximately the same x-ray dose or photon flow.

So that high-energy projections h also can be calculated in the angular ranges in which only low-energy projections l are acquired, the adjustment of voltage U and current l is provided such that, given two sets of successive rotations $R_n$, $R_{n+1}$ and $R_{n+1}$, $R_{n+2}$, during the second rotation $R_{n+1}$ or $R_{n+2}$ high-energy projections h are acquired in the angular ranges in which low-energy projections l were previously acquired in the first rotation $R_n$ or $R_{n+1}$.

FIG. 5 shows a sequence of low-energy projections l and high-energy projections h for different rotations $R_n$, $R_{n+1}$, $R_{n+2}$ in tabular form for the alternating adjustment of voltage U and current l from FIG. 4. The same angular ranges b1 and b2 and b3 exhibit different projections in successive rotations $R_n$, $R_{n+1}$, $R_{n+2}$. For example, high-energy projections h are acquired in the first angular range b1 in the n-th rotation $R_n$ while low-energy projections l are acquired in a successive n+1-th rotation $R_{n+1}$ for the same first angular range b1.

Figure 6:
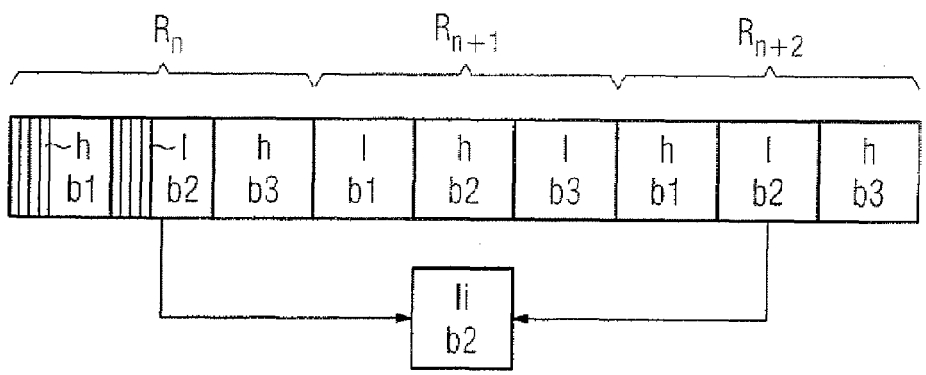
FIG. 6 shows an interpolated low-energy projection for the n+1-th rotation in a second angular range for the alternating adjustment of voltage and current of FIG. 4.

A low-energy projection can be interpolated for each high-energy projection on the basis of low-energy projections acquired in the same angular ranges from different rotations. As an example, FIG. 6 shows which projections from adjacent rotations are used for interpolation of a low-energy projection li, for example for the n+1-th rotation $R_{n+1}$ in the second angular range b2. The low-energy projections l of the n-th rotation $R_n$ is from the same second angular range b2, while the low-energy projections l of the n+2-th rotation $R_{n+2}$ are likewise from the same second angular range b2. The interpolation can be done, for example, by simple averaging of both low-energy projections. Artifacts in the interpolated low-energy projections li due to the geometric offset of the acquired image information can largely be prevented in the projections used for interpolation, by the scanning ensuing with a large image overlap between the projections from adjacent rotations.

Figure 7:
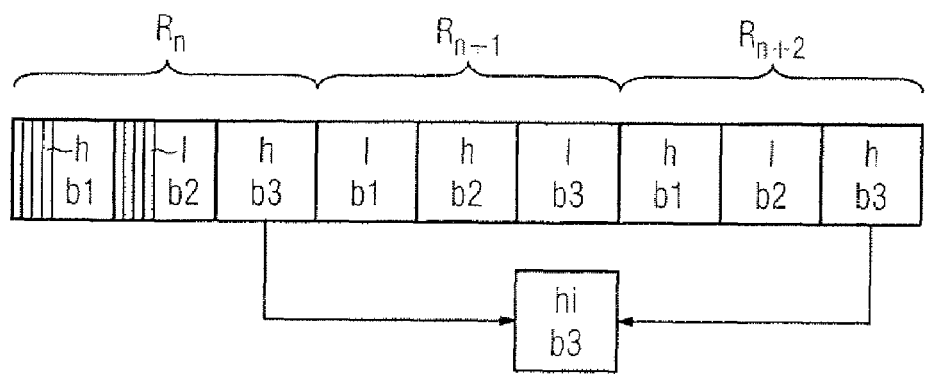
FIG. 7 shows interpolated high-energy projection for the n+1-th rotation in a third angular range for the alternating adjustment of voltage and current of FIG. 4.

A high-energy projection can be interpolated in the same manner for each low-energy projection on the basis of high-energy projections acquired in the same angular ranges from different rotations. As an example, FIG. 7 shows which projections from adjacent rotations are used for the calculation of the interpolated high-energy projections hi in the n+1-th rotation Rn+1 in the third angular range b3. The acquired and interpolated low-energy projections l, li and high-energy projections h, hi, enable a simple calculation (according to a known reconstruction method) of a low-energy image and of a high-energy image, each in the form of a slice or volume image.

A third operating mode likewise serves for detection of multiple energy images in the form of slice or volume images. In this operating mode the further adjustment variable is the exposure time instead of the current. The adjustment of voltage and exposure time ensues with a substantially constant current of the x-ray tube and a spiral scanning of the subject region. The adjustment device is operated such that one of the high-energy projections is respectively acquired at a set first voltage value and a set first exposure time and one of the low-energy projections is acquired at a set second voltage value and a set second exposure time, the high-energy projections and low-energy projections being acquired in an alternating fashion. Voltage values and exposure times are selected such that the x-ray radiation for the high-energy projections and for the low-energy projections essentially exhibits the same x-ray dose or photon flow.

Figure 8:
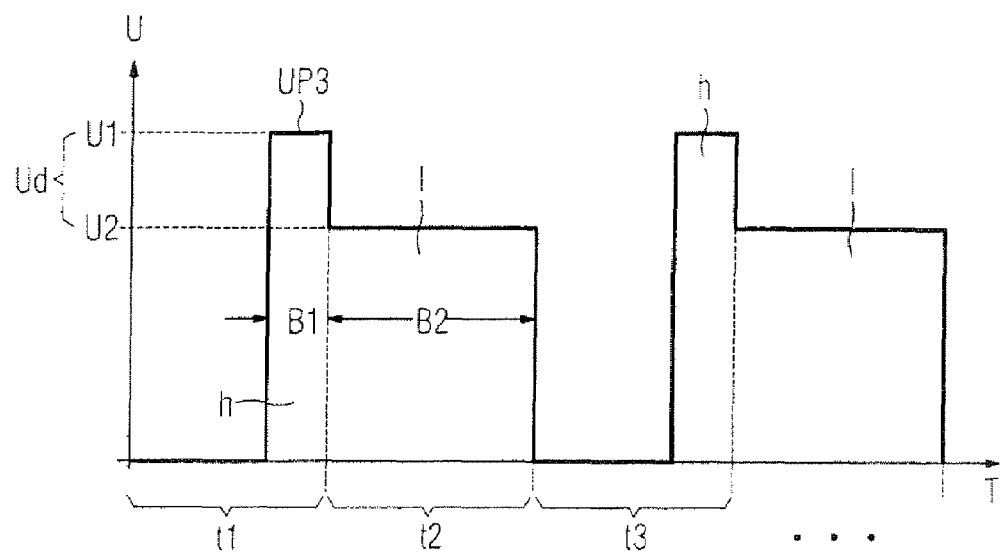
FIG. 8 shows alternating adjustment of voltage and exposure time in the tomography apparatus of FIG. 1, in the form of a third signal profile, wherein an adaptation of a first voltage value to a second voltage value directly ensues.

FIG. 8 shows an example of alternating adjustment of voltage and exposure time in the form of a third signal profile UP3. Starting from the set first voltage value U1 and the set first exposure time B1, the high-energy projection h is directly adapted to the second voltage value U2 and to the second exposure time B2 in the subsequent low-energy projections l.

The generation of a high-energy projection h ensues, for example, at a set first voltage value U1 of 140 kV and at a set first exposure time B1 of 60 μsec; in contrast to this, a low-energy projection l ensues, for example, at a set second voltage value U2 of 80 kV and at a set second exposure time B2 of 300 μsec, such that the x-ray radiation exhibits approximately the same x-ray dose or photon flow for both projections.

Figure 9:
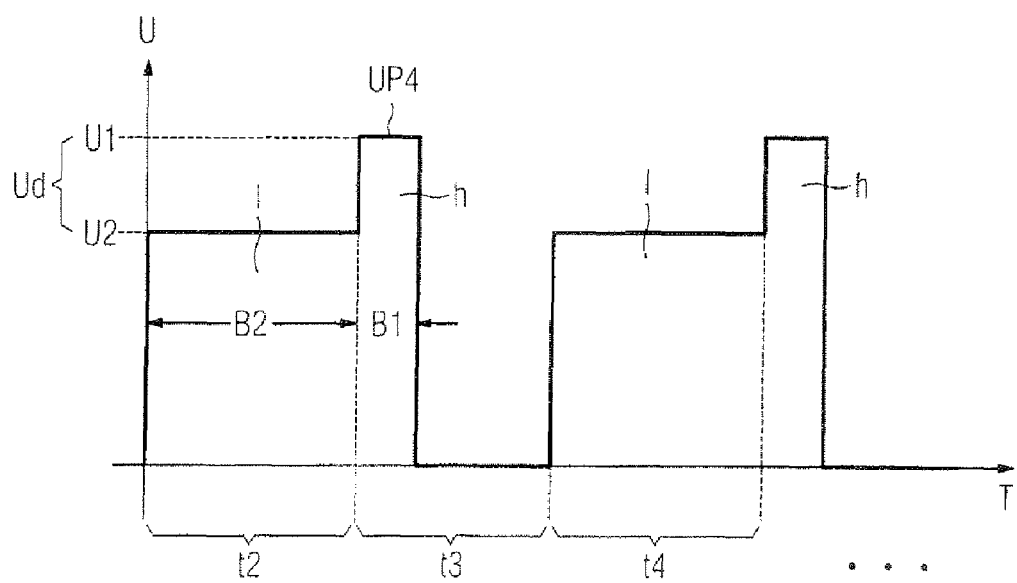
FIG. 9 shows alternating adjustment of voltage and exposure time in the form of a fourth signal profile, wherein an adaptation of the second voltage value to the first voltage value directly ensues.

FIG. 9 shows another example of alternating adjustment of voltage and exposure time in the form of a fourth signal profile UP4. Starting from the set second voltage value U2 and the set second exposure time B2, the low-energy projection l is directly adapted to the first voltage value U1 and to the first exposure time B1 in the subsequent high-energy projection n.

With such adjustments, at least in the case of one of the two changes between the control values, the voltage U must merely be adjusted by the difference Ud between the first voltage U1 and the second voltage U2, such that in particular a simpler operation of the high-voltage generator is ensured.

In the third operating mode, for each high-energy projection a low-energy projection is interpolated based on low-energy projections of the same rotation acquired at adjacent scan positions. A high-energy projection is interpolated corresponding to each low-energy projection.

Figure 10:
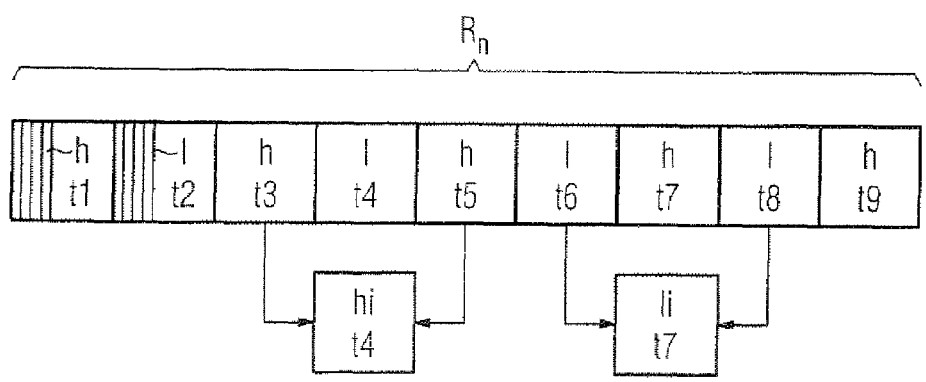
FIG. 10 shows an interpolation of a high-energy projection and a low-energy projection in the form of a block diagram for the alternating adjustment of voltage and exposure time of FIG. 8 or 9.

An interpolation of the low-energy projection li at the seventh scan position t7 of the n-th rotation $R_n$, which interpolation is based on low-energy projections l of the same rotation acquired at the sixth scan position t6 and the eighth scan position t8, is shown as an example in FIG. 10. Moreover, an interpolation of the high-energy projection li at the fourth scan position t4 is also exemplarily indicated in the same FIG. 10, this interpolation being formed based on high-energy projections h for the same rotation and acquired at the third scan position t3 and at the fifth scan position t5. The acquired and interpolated low-energy projections l, li and high-energy projections h, hi enable a simple calculation (according to a known reconstruction method) of a low-energy image and a high-energy image, each in the form of a slice or volume image.

Figure 11:
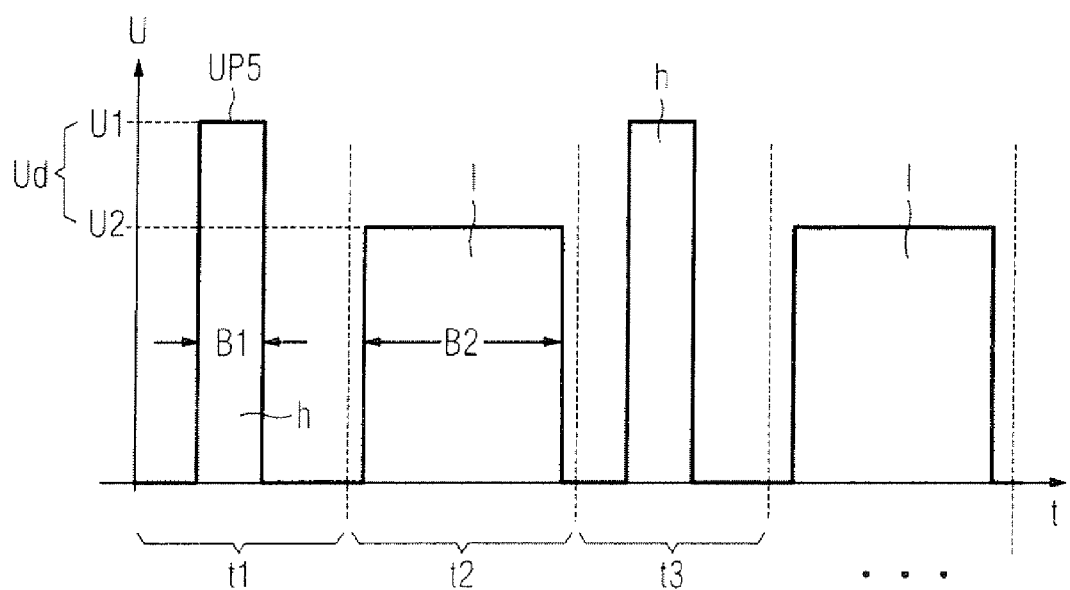
FIG. 11 show alternating adjustment of voltage and exposure time in the tomography apparatus of FIG. 1, in the form of a fifth signal profile, wherein the time interval of the exposure time is centered with regard to the time interval of a respective projection.

FIG. 11 shows an example of alternating adjustment of voltage and exposure time in the form of a fifth signal profile UP3. Such an adjustment is particularly advantageous for grid-controlled x-ray tubes in which a fast adjustment is possible, both of the energy of the x-ray radiation and of the x-ray dose connected with the x-ray radiation. In this adjustment, the first exposure time B1 is centered with regard to the time interval of a scan given a set first voltage value U1 and the second exposure time B2 is centered with regard to the time interval of a scan given a set second voltage value U2. By such a centered alignment of the time interval of the exposure times with regard to the time interval of a respective projection it is ensured that all low-energy projections l and high-energy projections h are acquired at equidistant intervals.

In addition to grid-controlled x-ray tubes, x-ray tubes with a field emission electron source or a photo-cathode electron source also can be used for this adjustment of voltage U and exposure time B. Laser-generated plasma x-ray radiators also can be used.

Figure 12:
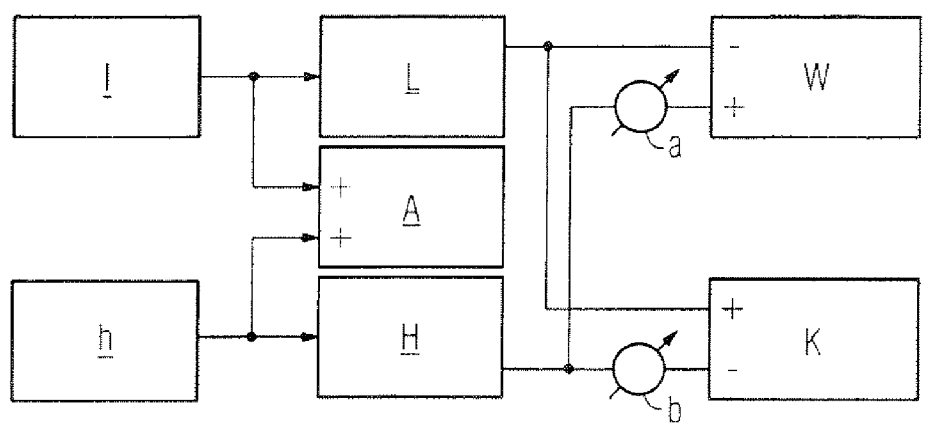
FIG. 12 illustrates a calculation of soft tissue and osseous tissue as well as the calculation of an additive image in the form of a flowchart.

In addition to the high-energy image and the low-energy image, in each operating mode further result images can be calculated which, for example, can support a physician making a diagnosis. FIG. 12 shows a flowchart for calculation of a soft tissue image W, an osseous tissue image K and an additive image A on the basis of acquired high-energy projections h and low-energy projections l. In a first step, the high-energy projections h acquired during the scanning of a subject region are further processed into a high-energy image H and the acquired low-energy projections l are further processed into a low-energy image L. The additive image A can be calculated by means of an addition of the respective high-energy projection h with the respective low-energy projection l. The soft tissue image W is formed from the high-energy image H (weighted with a first weighting coefficient a) by subtraction of the low-energy image L. In contrast to this, the osseous tissue image K is determined from the low-energy image L by subtraction of the high-energy image H (weighted with a second weighting coefficient b).

The first weighting coefficient a for calculation of the soft tissue image W can be, for example, 1.5 and the second weighting coefficient b for calculation of the bony tissue image K can be 1.25. The corresponding weighting coefficients a, b, however, can be predetermined or changed by operating personnel as an adjustment of the achievable image quality.

Although modifications and changes may be suggested by those skilled in the art, it is the intention of the inventor to embody within the patent warranted hereon all changes and modifications as reasonably and properly come within the scope of his contribution to the art.

I claim as my invention:

1. A tomography apparatus comprising:
    an acquisition system adapted to interact with a subject to acquire projections of a region of the subject, said acquisition system comprising an x-ray radiator that emits x-rays with an x-ray dose predetermined by a voltage supplied to the x-ray radiator, a current supplied to the x-ray radiator, and an exposure time during which the x-ray radiator emits said x-rays;
    a first control unit connected to the x-ray radiator that alternatingly adjusts said voltage between a first voltage value for acquisition of high-energy projections and a second voltage value, differing from said first voltage value, for acquisition of low-energy projections;
    a second control unit connected to said x-ray radiator that alternatingly adjusts a further control variable for operating said x-ray radiator between a first control value associated with said first voltage value and a second control value, differing from said first control value, associated with said second voltage value; and
    an adjustment device connected to said first control unit and to said second control unit that adjusts said first control value dependent on said first voltage value and adjusts said second control value dependent on said second voltage value to cause said x-rays emitted by said x-ray radiator to have a substantially equal x-ray dose during acquisition of said high energy projections and during acquisition of said low energy projections.

2. A tomography apparatus as claimed in claim 1 wherein said acquisition system has a system axis, and comprising a displacement mechanism that produces a relative displacement along said system axis between said acquisition system and the subject during acquisition of said projections.

3. A tomography apparatus as claimed in claim 2 comprising a rotational drive engaging said acquisition system to rotate said acquisition system around said system axis during acquisition of said projections.

4. A tomography apparatus as claimed in claim 1 wherein said control unit adjusts said exposure time, with said current substantially constant, as said further control variable.

5. A tomography apparatus as claimed in claim 4 wherein said acquisition system has a system axis and comprising a displacement mechanism that produces a relative displacement between said region of said subject and said acquisition system, and wherein said first control unit and said second control unit respectively alternatingly adjust said voltage and said exposure time during said relative displacement for acquisition of said high-energy projections and said low-energy projections.

6. A tomography apparatus as claimed in claim 5 comprising a rotational drive engaging said acquisition system to rotate said acquisition system around said system axis, and wherein said first control unit and said second control unit respectively alternatingly adjust said voltage and said exposure time during simultaneous relative displacement between said subject region and said acquisition system, and rotation of said acquisition system, and wherein one of said high-energy projections is acquired with a set first voltage value and a set first exposure time, and wherein one of said low-energy projections is acquired with a set second voltage value and a set second exposure time, said high-energy projections and said low-energy projections being alternatingly acquired.

7. A tomography apparatus as claimed in claim 6 wherein said first control unit directly adapts said second voltage value to said set first voltage value, for a low-energy projection acquired subsequently to said one of said high-energy projections, and wherein said second control unit directly adapts said second exposure time to said set first exposure time for acquisition of said low-energy projection subsequently to said one of said high-energy projections.

8. A tomography apparatus as claimed in claim 6 wherein said first control unit directly adapts said first voltage value to said set second voltage value for a high-energy projection acquired subsequently to said one of said low-energy projections, and wherein said second control unit directly adapts said first exposure time to said set second exposure time for acquisition of said high-energy projection subsequently to said one of said low-energy projections.

9. A tomography apparatus as claimed in claim 6 wherein said second control unit centers said first exposure time relative to a time interval of a projection obtained with said set first voltage value, and centers said second exposure time relative to a time interval of a projection acquired with said set second voltage value.

10. A tomography apparatus as claimed in claim 6 wherein each of said projections is acquired at a projection angle during rotation of said acquisition system, and wherein said acquisition system comprises a radiation detector that generates projection data for each of said projections, and comprising a computer, supplied with said projection data that, for each high-energy projection acquired at a high-energy projection angle at which a low-energy projection was not acquired, interpolating a low-energy projection for said high-energy projection angle using projection data from respective low energy projections acquired at projection angles adjacent said high-energy projection angle in a same rotation of said acquisition system.

11. A tomography apparatus as claimed in claim 10 wherein said computer calculates a low-energy image from the acquired low-energy projections and the interpolated low-energy projections.

12. A tomography apparatus as claimed in claim 6 wherein each of said projections is acquired at a projection angle during rotation of said acquisition system, and wherein said acquisition system comprises a radiation detector that generates projection data for each of said projections, and comprising a computer, supplied with said projection data that, for each high-energy projection acquired at a low-energy projection angle at which a high-energy projection was not acquired, interpolating a high-energy projection for said low-energy projection angle using projection data from respective high-energy projections acquired at projection angles adjacent said low-energy projection angle in a same rotation of said acquisition system.

13. A tomography apparatus as claimed in claim 12 wherein said computer calculates a high-energy image from the acquired high-energy projections and the interpolated high-energy projections.

14. A tomography apparatus as claimed in claim 1 wherein said second control unit adjusts said current, with said exposure time substantially constant, as said further control variable.

15. A tomography apparatus as claimed in claim 14 wherein said acquisition system has a system axis, and comprising a displacement mechanism that a produces a relative displacement between said region of said subject and said acquisition system along said system axis, and a rotational drive engaging said acquisition system to rotate said acquisition system around said system axis through a plurality of angular ranges, and wherein said acquisition system acquires a plurality of successive high-energy projections with a set first voltage value and a set first current value and a plurality of successive low-energy projections with a set second voltage value and a set second current value, said high-energy projections and said low-energy projections being alternatingly acquired in different angular ranges.

16. A tomography apparatus as claimed in claim 15 wherein said acquisition system, in two sets of successive rotations, acquires high-energy projections during a first rotation and low-energy projections during a second rotation in substantially the same angular range.

17. A tomography apparatus as claimed in claim 15 wherein said acquisition system, in two sets of successive rotations, acquires low-energy projections during a first rotation and high-energy projections during a second rotation in substantially the same angular range.

18. A tomography apparatus as claimed in claim 15 wherein each projection is acquired in an angular range, and wherein said acquisition system comprises a radiation detector that generates projection data for each projection, and comprising a computer supplied with said projection data, said computer, for each high-energy projection acquired at a high-energy angular range in a rotation of said acquisition system interpolates a low-energy projection for that rotation from projection data respectively for low-energy projections acquired in said high-energy angular range in other rotations of said acquisition system.

19. A tomography apparatus as claimed in claim 15 wherein each projection is acquired at a projection angle, and wherein said acquisition system comprises a radiation detector that generates projection data for each projection, and comprising a computer supplied with said projection data, said computer, for each low-energy projection acquired at a low-energy angular range in a rotation of said acquisition system interpolates a high-energy projection for that rotation from projection data respectively for high-energy projections acquired in said low-energy angular range in different rotations of said acquisition system.

20. A tomography apparatus as claimed in claim 1 comprising a computer supplied with said low-energy projections and said high-energy projections, said computer calculating a low-energy image L from low-energy projections and calculating a high-energy image H from high-energy projections, and calculating a soft tissue image W=a*H−L, wherein a is a weighting coefficient for said high-energy image.

21. A tomography apparatus as claimed in claim 1 comprising a computer supplied with said high-energy projections and said low-energy projections, said computer calculating a low-energy image L from said low-energy projections and calculating a high-energy image H from said high-energy projections, and calculating an osseous tissue image K=L−b*H, wherein b is a weighing coefficient for said high-energy image.

22. A tomography apparatus as claimed in claim 1 comprising a computer supplied with said high-energy projections and said low-energy projections, said computer calculating a high-energy image from said high-energy projections and a low-energy image from said low-energy projections, and calculating an additive image by adding said high-energy image and said low-energy image.

23. A tomography apparatus as claimed in claim 1 comprising a computer supplied with said low-energy projections and said high-energy projections, said computer calculating a conventional CT image from said low-energy projections and said high-energy projections.

24. A method for operating a tomography apparatus comprising the steps of:
acquiring projections of a region of the subject with an acquisition system comprising an x-ray radiator that emits x-rays with an x-ray dose predetermined by a voltage supplied to the x-ray radiator, a current supplied to the x-ray radiator, and an exposure time during which the x-ray radiator emits said x-rays;
with a first control unit connected to the x-ray radiator, alternatingly adjusting said voltage between a first voltage value for acquisition of high-energy projections and a second voltage value, differing from said first voltage value, for acquisition of low-energy projections;
with a second control unit connected to said x-ray radiator, alternatingly adjusting a further control variable for operating said x-ray radiator between a first control value associated with said first voltage value and a second control value, differing from said first control value, associated with said second voltage value; and
adjusting said first control value dependent on said first voltage value and adjusting said second control value dependent on said second voltage value to cause said x-rays emitted by said x-ray radiator to have a substantially equal x-ray dose during acquisition of said high energy projections and during acquisition of said low energy projections.

25. A method as claimed in claim 24 wherein said acquisition system has a system axis, and comprising producing a relative displacement along said system axis between said acquisition system and the subject during acquisition of said projections.

26. A method as claimed in claim 25 comprising rotating said acquisition system around said system axis during acquisition of said projections.

27. A method as claimed in claim 24 comprising adjusting said exposure time, with said current substantially constant, as said further control variable.

28. A method as claimed in claim 27 wherein said acquisition system has a system axis and comprising producing a relative displacement between said region of said subject and said acquisition system, and comprising, with said first control unit and said second control unit, alternatingly adjusting said voltage and said exposure time during said relative displacement for acquisition of said high-energy projections and said low-energy projections.

29. A method as claimed in claim 28 comprising rotating said acquisition system around said system axis, and comprising with said first control unit and said second control unit, alternatingly adjusting said voltage and said exposure time during simultaneous relative displacement between said subject region and said acquisition system, and rotation of said acquisition system, and acquiring one of said high-energy projections with a set first voltage value and a set first exposure time, and acquiring one of said low-energy projections with a set second voltage value and a set second exposure time, said high-energy projections and said low-energy projections being alternatingly acquired.

30. A method as claimed in claim 29 comprising, in said first control unit, directly adapting said second voltage value to said set first voltage value, for a low-energy projection acquired subsequently to said one of said high-energy projections, and, in said second control unit directly adapting said second exposure time to said set first exposure time for acquisition of said low-energy projection subsequently to said one of said high-energy projections.

31. A method as claimed in claim 29 comprising, in said first control unit, directly adapting said first voltage value to said set second voltage value for a high-energy projection acquired subsequently to said one of said low-energy projections, and wherein said second control unit directly adapts said first exposure time to said set second exposure time for acquisition of said high-energy projection subsequently to said one of said low-energy projections.

32. A method as claimed in claim 29 comprising, in said second control unit, centering said first exposure time relative to a time interval of a projection obtained with said set first voltage value, and centering said second exposure time relative to a time interval of a projection acquired with said set second voltage value.

33. A method as claimed in claim 29 comprising, acquiring each of said projections at a projection angle during rotation of said acquisition system, and wherein said acquisition system comprises a radiation detector that generates projection data for each of said projections, and comprising, in a computer supplied with said projection data, interpolating for each high-energy projection acquired at a high-energy projection angle at which a low-energy projection was not acquired, a low-energy projection for said high-energy projection angle using projection data from respective low energy projections acquired at projection angles adjacent said high-energy projection angle in a same rotation of said acquisition system.

34. A method as claimed in claim 33 comprising, in said computer, calculating a low-energy image from the acquired low-energy projections and the interpolated low-energy projections.

35. A method as claimed in claim 29 comprising acquiring each of said projections at a projection angle during rotation of said acquisition system, and wherein said acquisition system comprises a radiation detector that generates projection data for each of said projections, and comprising, in a computer supplied with said projection data, interpolating for each high-energy projection acquired at a low-energy projection angle at which a high-energy projection was not acquired, a high-energy projection for said low-energy projection angle using projection data from respective high-energy projections acquired at projection angles adjacent said low-energy projection angle in a same rotation of said acquisition system.

36. A method as claimed in claim 35 comprising, in said computer calculating a high-energy image from the acquired high-energy projections and the interpolated high-energy projections.

37. A method as claimed in claim 24 comprising, in said control unit, adjusting said current, with said exposure time substantially constant, as said further control variable.

38. A method as claimed in claim 37 wherein said acquisition system has a system axis, and comprising producing a relative displacement between said region of said subject and said acquisition system along said system axis, and rotating said acquisition system around said system axis through a plurality of angular ranges, and acquiring a plurality of successive high-energy projections with a set first voltage value and a set first current value and a plurality of successive low-energy projections with a set second voltage value and a set second current value, said high-energy projections and said low-energy projections being alternatingly acquired in different angular ranges.

39. A method as claimed in claim 38 comprising, in two sets of successive rotations, acquires high-energy projections during a first rotation and low-energy projections during a second rotation in substantially the same angular range.

40. A method as claimed in claim 38 comprising, in two sets of successive rotations, acquiring low-energy projections during a first rotation and high-energy projections during a second rotation in substantially the same angular range.

41. A method as claimed in claim 38 comprising acquiring each projection in an angular range, and wherein said acquisition system comprises a radiation detector that generates projection data for each projection, and comprising, in a computer supplied with said projection data, interpolating, for each high-energy projection acquired at a high-energy angular range in a rotation of said acquisition system, a low-energy projection for that rotation from projection data respectively for low-energy projections acquired in said high-energy angular range in other rotations of said acquisition system.

42. A method as claimed in claim 38 comprising acquiring each projection in an angular range, and wherein said acquisition system comprises a radiation detector that generates projection data for each projection, and comprising a computer supplied with said projection data, interpolating, for each low-energy projection acquired at a low-energy angular range in a rotation of said acquisition system, a high-energy projection for that rotation from projection data respectively for high-energy projections acquired in said low-energy angular range in other rotations of said acquisition system.

43. A method as claimed in claim 24 comprising, in a computer supplied with said low-energy projections and said high-energy projections, calculating a low-energy image L from low-energy projections and calculating a high-energy image H from high-energy projections, and calculating a soft tissue image W=a*H−L, wherein a is a weighting coefficient for said high-energy image.

44. A method as claimed in claim 24 comprising, in a computer supplied with said high-energy projections and said low-energy projections, calculating a low-energy image L from said low-energy projections and calculating a high-energy image H from said high-energy projections, and calculating an osseous tissue image K=L−b*H, wherein b is a weighing coefficient for said high-energy image.

45. A method as claimed in claim 24 comprising, in a computer supplied with said high-energy projections and said low-energy projections, calculating a high-energy image from said high-energy projections and a low-energy image from said low-energy projections, and calculating an additive image by adding said high-energy image and said low-energy image.

46. A method as claimed in claim 24 comprising, in a computer supplied with said low-energy projections and said high-energy projections, calculating a conventional CT image from said low-energy projections and said high-energy projections.

* * * * *